United States Patent [19]

Kanai

[11] 4,386,159
[45] May 31, 1983

[54] METHOD OF PRODUCING METHANE

[76] Inventor: Masakuni Kanai, No. 1-5-601, Arai 1-chome, Nakano-ku, Tokyo-to, Japan

[21] Appl. No.: 225,105

[22] Filed: Jan. 14, 1981

[51] Int. Cl.$^3$ .............................................. C12P 5/02
[52] U.S. Cl. .................................. 435/167; 435/801; 210/603
[58] Field of Search ...................... 435/166, 167, 801; 210/603

[56] References Cited

U.S. PATENT DOCUMENTS 3,981,800  9/1976  Ort ..................................... 210/603
4,022,665  5/1977  Gosh et al. ......................... 435/167

OTHER PUBLICATIONS

Nelson et al. "Effect of Temperature of Digestion, Chemical Composition & Size of Particles on Production of Fuel Gas from Farm Wastes", J. Ag. Res. vol. 58 (1939) pp. 273–287.

Primary Examiner—R. B. Penland
Attorney, Agent, or Firm—Steinberg & Raskin

[57] ABSTRACT

Methane is produced by fermentation of organic material, wherein the organic material is finely ground to an average particle size of less than 3 mm, mixed with a seed sludge containing bacteria which decomposes the organic material to methane, and the mixture maintained at a temperature which promotes the decomposition of the organic material to methane by the bacteria.

13 Claims, 3 Drawing Figures

METHOD OF PRODUCING METHANE

BACKGROUND OF THE INVENTION

Natural organic waste matters such as garbage, sewage sludge, pulp industry sludge, waste matter from primary industries and farming and fishing villages, and waste matter from food factories, have been subjected to anaerobic decomposition in fermentation tanks containing methane bacteria, and the methane gas generated in the tanks have been recovered. However, such anaerobic decomposition has generally been quite inefficient because of the very long period of time (generally longer than 30 days) required to attain a equilibrium stage in the methane fermentation. This is due to the fact that anaerobic decomposition comprises two stages, namely: (1) acid fermentation, and (2) methane fermentation.

SUMMARY OF THE INVENTION

Generally speaking in accordance with the present invention organic material, generally waste matter, is finely ground to an average particle size of less than 3 mm, mixed with a seed sludge containing bacteria which decomposes the organic material to methane, and maintained at a temperature which promotes the decomposition of the organic material by the bacteria to produce methane.

The method of the invention effects stable methane fermentation without requiring any energy for agitation, the fermentation being accomplished in short periods of time.

I have found that the acid fermentation period in the production of methane can be reduced considerably and the methane fermentation immediately effected by grinding the organic material to an average particle size of less than 3 mm, which results in conversion of the material to a juice-like liquid. According to the prior art, the particle diameter was about 10 mm or greater, and by proceeding in accordance with the present invention, it has been found that methane gas is formed in remarkably increased quantities, which is further improved by carrying out the methane fermentation in a positive $CO_2$ atmosphere.

It is accordingly a primary object of the present invention to provide a process for methane fermentation wherein the acid fermentation period is drastically reduced and the entire period of time required for completion of the methane fermentation is reduced to about 1/6 of that required according to the prior art.

It is another object of the present invention to provide a process for methane fermentation by which the yield of the methane gas is considerably improved.

It is still another object of the present invention to provide a process for methane fermentation without the need for agitation, thus considerably saving energy which is required for agitation according to the prior art in methane fermentation.

Other objects and advantages of the present invention will be apparent from a further reading of the specification and of the appended claims.

With the above and other objects in view, the present invention mainly comprises a process for methane fermentation, wherein an organic material is finely ground to an average particle size of less than 3 mm, the ground material mixed with a seed sludge for the methane fermentation, and the mixture maintained at a temperature to promote the decomposition of the organic material by the bacteria.

According to a further embodiment of the invention, methane fermentation is carried out in a positive $CO_2$ atmosphere, which improves the yield of the gaseous methane.

The present invention further comprises the embodiment wherein a phosphate buffer solution is added to the liquid mixture to control the pH thereof.

Among the most suitable of the organic materials which are treated for the production of methane in accordance with the present invention are natural organic waste matters such as garbage, sewage sludge, pulp industry sludge, waste matter from primary industries and farming and fishing villages, and waste matters from food factories.

The organic waste matter containing solids is finely ground to an average particle diameter of less than 3 mm by means of a comminuter or the like to obtain a juice like liquid.

According to the preferred embodiment of the present invention, the particle size should be as small as possible, and under all circumstances less than 3 mm. For example, it is preferred that the waste matter be ground so that more than 50% by weight of the particles has a diameter of less than 2.5 mm and more than about 40% by weight of the particles has a diameter of less than 1.5 mm. Thus, for example, the waste matter may be ground so that 46% by weight of the particles pass through a 2.38 mm mesh sieve and 30% by weight of the particles pass through a 1.19 mm mesh sieve, according to the wet sieving method.

It is extremely important according to the invention to grind the organic material into fine particles. One of the reasons for this is that the thus comminuted organic material has an increased surface area which is acted upon in the method, thereby facilitating the decomposition thereof. This technique has been developed on the basis of the confirmation of the fact that if the material is ground into fine particles, water eluted from the broken fibers accelerates the action of the enzymes and putrefactive bacteria so that the material is immediately decomposed into organic acids and the gasification by means of the methane bacteria is accelerated.

In the treatment of the ground organic material, it has been found that the anaerobes exhibit the highest activity, and therefore the fresh cells are formed in the largest amount when the C/N ratio of the material to be decomposed is in the range of about 12–16:1. It is therefore preferred to select as the waste matter for decomposition such waste matter that has a C/N ratio in the range of about 12–16:1. The C/N ratio is the carbon:nitrogen ratio.

Thus, for example, if a mixture of a slude having a high protein content and waste vegetables or fallen leaves having a high carbohydrate content is digested, the gas generated is much greater in amount than that obtained when the same are digested separately.

It is thus preferred according to the present invention to obtain the most suitable C/N ratio for the action of the anaerobe by mixing sludge of low C/N ratio with organic waste matter having a high C/N ratio.

The process of the present invention is carried out in principle by so called high temperature fermentation. The temperature maintained during the fermentation is preferably between about 50°–60° C. from the standpoint of reliability of the reaction, and most preferably at a temperature of about 52°–55° C. from the standpoint of bacterial activity. The effects of the invention can also be obtained by intermediate temperature fermentation (30–37° C.), however, the efficiency is somewhat lower.

An important aspect of the present invention, which differs from conventional processes for production of methane by fermentation, is that according to the present invention the reaction system is not agitated during the fermentation. It has been found quite surprisingly that agitation during fermentation results in an accumulation of organic acids which inhibits the reaction. On the other hand, if the process is carried out without agitation, as in accordance with the present invention, the anaerobes act most effectively on the organic material to provide highly effective decomposition thereof.

As the seed sludge for use in methane fermentation, seed sludges containing known methane bacteria such as digestion sludge obtained after an acclimatization period in a fermentation tank in a sewage disposal plant may be used.

The amount of the organic material to be treated is preferably in the range of 30–400 g, most preferably 100–300 g per liter of the seed sludge.

The dry weight of the organic material in the liquid mixture of the finely pulverized material and the seed sludge is preferably about 1–10% by weight. Accordingly, water may be supplemented if necessary, depending on the seed sludge and organic materials used.

According to the preferred embodiment of the invention, the methane fermentation is effected in a positive $CO_2$ atmosphere and this process may roughly be divided into two processes. One of the processes comprises placing the liquid mixture in a closed fermentation tank and charging gaseous $CO_2$ into the space above the mixture to obtain an oxygen free condition. The other process comprises feeding a $CO_2$-containing liquid directly into the liquid mixture. The $CO_2$ feeding may be effected either continuously or intermittently to effect the fermentation in a $CO_2$ atmosphere in both cases. A $CO_2$-containing liquid formed during the methane fermentation may be used effectively by recovering and recycling the same as the $CO_2$-containing liquid for direct feeding into the liquid mixture.

If the $CO_2$-containing liquid or recycling liquid is compressed under a pressure of about 1–30 Kg/cm$^2$ for elevating the $CO_2$ content thereof and then returned to the fermentation tank, fine $CO_2$ bubbles are formed when it is placed under atmospheric pressure. The bubbles adhere to the bacteria or other substrate particles to accelerate the reaction of the $CO_2$ according to the present invention, which will be described below.

It is preferred in the present invention to maintain the liquid mixture in the pH range of 7.4–8.0. If necessary, a phosphate buffer solution is added to the liquid mixture for pH adjustment. As the phosphate buffer solution, there may be used, for example, a composition comprising x ml of 0.2 mol aqueous $KH_2PO_4$ solution and y ml of 0.2 mol aqueous NaOH solution. These are mixed with z ml of the liquid mixture to adjust the pH in the range of 7.4–8.0 to further accelerate the methane fermentation.

The preferred proportion of x, y and z in the mixture is approximately as follows:

$$y+z=3x$$

This proportion is not critical; there is some tolerance (for example, ±20%) as a matter of course. The pH of the liquid mixture is adjusted to a suitable value within said range by controlling the quantity (y ml) of the 0.2 mol aqueous NaOH solution.

For example, for obtaining a pH in the range of 7.4–8.0, it is preferred to determine x and y in the following relative quantities:

$$x=(0.45-0.49)z$$

$$y=(0.36-0.46)z.$$

There is a tolerance (for example, ±20%) in this proportion.

BRIEF DESCRIPTION OF THE DRAWINGS

For a fuller understanding of the invention, reference is had to the following description taken in connection with the accompanying drawings, in which.

DESCRIPTION OF PREFERRED EMBODIMENTS

The following examples, which are given in connection with a fuller description of the drawings, are given to further illustrate the present invention. The scope of the invention, is not, however, meant to limited to the specific details of the examples:

EXAMPLE 1

Figure 1:
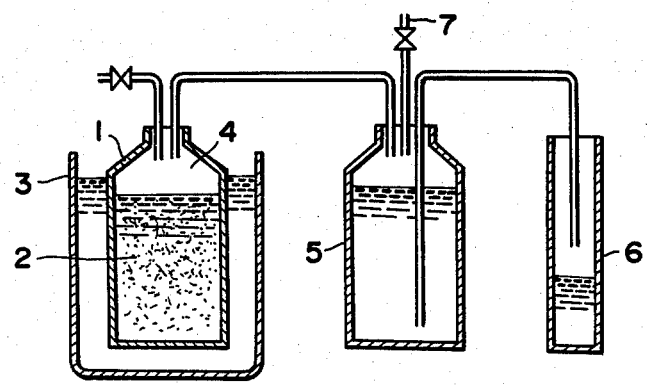
FIG. 1 schematically shows a device for carrying out the process of the present invention.

A mixture 2 comprising an organic material (vegetable garbage finely ground into a juice-like liquid), a seed sludge for the methane fermentation and, if necessary, water is charged into fermentation tank 1 shown in FIG. 1. The tank 1 was placed in a constant temperature bath 3 and kept within a predetermined temperature range to effect the methane fermentation without agitation.

Gaseous methane formed by the methane fermentation was collected in collecting tank 5. The amount of the gaseous methane thus collected was measured by means of a measuring cylinder 6 and taken out through an opening 7 and stored in a storage vessel (not shown).

The fermentation tank 1 had a volume of 3 liters. As the seed sludge for the methane fermentation, 2 liters of a digested sludge which had been fermented in a fermentation tank in a sewage disposal plant at 40° C. for about 12 days were used. As the organic material to be charged, 200 g of cabbage finely ground into particles of an average particle diameter of less than 2.5 mm were added thereto to obtain the liquid mixture 2 having a water content of 90%. The contents of the fermentation tank 1 were kept at 53°–54° C. by means of the constant temperature bath 3 to effect the methane fermentation. During the fermentation, no agitation was effected.

As a result of the treatment, the liquid mixture was separated into three layers, i.e. top scum layer, intermediate layer of water separated out and the bottom sludge layer in the fermentation tank. The organic matter incorporated therein formed a layer below the scum, which was gradually decomposed by aerobes, thereby gasified to reduce the volume thereof as the fermentation proceeded. From this fact, it was considered that the vigorous methane fermentation proceeded below the scum.

Figure 2:
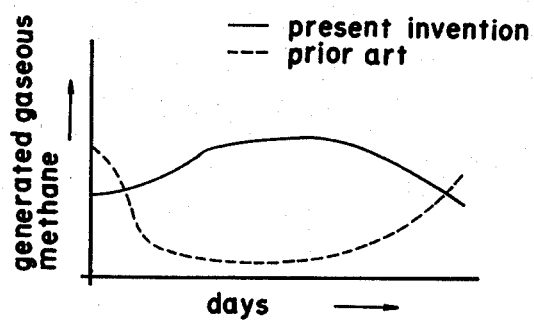
FIG. 2 is a graph showing methane production conditions according to the present invention in comparison with a conventional process wherein the organic material used is ground to a particle diameter of about 10 mm.

The results are shown in FIG. 2 in comparison with those obtained by a known process wherein the organic material (cabbage) ground into particles of an average diameter of 10 mm was used under the same conditions. It is apparent from FIG. 2 that there is a clear difference in the time of initiation of the effective methane fermentation. Thus, according to the process of the present invention, the vigorous methane fermentation proceeded even in the initial stage and pH was hardly lowered. This fact suggests that the acid fermentation period substantially disappeared.

EXAMPLE 2

The methane fermentation was effected under the same conditions as in Example 1 except that gaseous $CO_2$ was charged forcedly in an upper space 4 in the fermentation tank 1 to realize oxygen-free condition in space 4 so that the surface of the liquid mixture 2 was kept in contact with $CO_2$ during the methane fermentation reaction.

Figure 3:
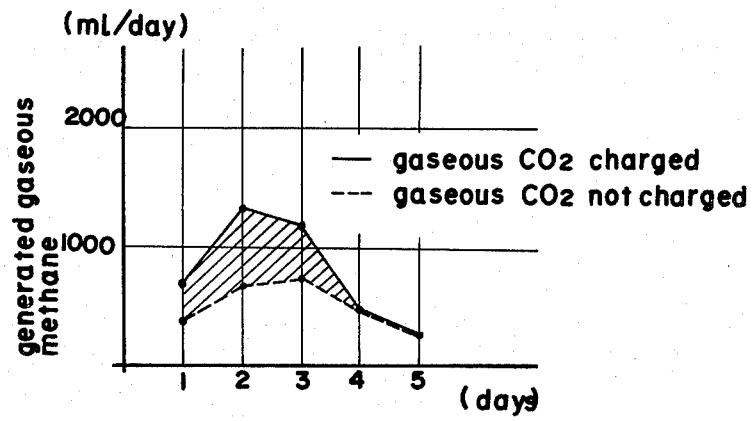
FIG. 3 is a graph showing the amount of gaseous methane formed by the process of the present invention in comparison with that formed by a conventional process without the charging of gaseous $CO_2$.

The results are shown in FIG. 3 in comparison with those obtained without the forced charging of gaseous $CO_2$.

It is apparent from FIG. 3 that a clear difference is recognized in the initial and intermediate periods. Thus, according to the process of the present invention, the vigorous, rapid methane fermentation proceeded even in the initial stage and an improvement in yield of gaseous methane (about 1400 ml per gram of the organic material contained in the starting material. The above amount of gaseous methane generated exclude the gas generated from the seed sludge per se.

It is considered that these effects are obtained because the methane gas generation was accelerated by the following reactions of the organic acids, hydrogen and alcohol (formed by the decomposition of the organic material) with $CO_2$ forcedly supplied:

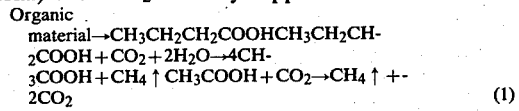
(1)

(2)

(3)

When organic materials are decomposed, methane and carbon dioxide are formed. It is considered that carbon dioxide thus formed exerts a great influence on the propagation of methane bacteria.

A reason therefor is that carbon dioxide is utilized when large molecules are decomposed into small molecules. Therefore, if carbon dioxide is charged forcedly above the liquid surface in the fermentation tank 1, carbon dioxide is reduced by the methane bacteria when the organic material rises to directly below the scum and is adhered to the scum. Consequently, the organic material is rapidly decomposed to form methane more effectively.

According to the process of the present invention, the initial acid fermentation period which requires about 30 days in general in conventional processes can be substantially omitted by finely grinding the organic material into particles of an average diameter of, for example, less than 3 mm to form a juice-like liquid before it is added to the seed sludge for the methane fermentation to form the liquid mixture, unlike conventional processes wherein the organic material is ground into particles of an average diameter of about 10 mm. The process is further improved by carrying out the reaction forcedly with $CO_2$ to accelerate fermentation. Furthermore, the period of methane fermentation (10–15 days in conventional processes) can be reduced to about 7 days. Therefore, the entire process can be completed in about 5–7 days, which period is about 1/6 of that required in conventional processes (40–45 days). In addition, the amount of gaseous methane can be increased to 1.5–2 times as much as that obtained by the conventional processes.

While the invention has been described in particular with respect to specific embodiments, it is apparent that variations and modification thereof can be made.

What is claimed is:

1. Method of producing methane by fermentation of organic material, which comprises finely grinding an organic material having a C/N ratio in the range of about 12–16:1 to an average particle size of less than 3 mm, mixing the finely ground organic material in a fermentation tank and effecting fermentation in a sole fermentation step with a fermentation sufficient amount of an aqueous seed sludge containing bacteria which decomposes said organic material to methane to form a liquid mixture and maintaining the thus obtained liquid mixture in said fermentation tank during said fermentation without agitation in a $CO_2$ atmosphere substantially free of oxygen, said atmosphere obtained by force charging $CO_2$ above the surface of the liquid mixture at a temperature which promotes decomposition of said organic material by said bacteria to produce methane while maintaining a pH of between about 7.4 and 8.0, whereby a top scum layer is formed below which is a layer of the finely ground organic material said organic material being decomposed by the bacteria to methane.

2. Method according to claim 1 wherein said organic material is a natural organic waste material.

3. Method according to claim 2 wherein said organic material is finely ground to a particle size such that 50% of the particles are of a size of less than 2.5 mm and more than 40% of the particles are of a particle size of less than 1.5 mm.

4. Method according to claim 3 wherein about 30–400 g/l of organic material is mixed per each liter of the seed sludge.

5. Method according to claim 4 wherein the dry weight of the organic material is about 1–10% of the liquid mixture.

6. Method according to claim 2 wherein said temperature is between about 50°–60° C.

7. Method according to claim 2 wherein said temperature is between 30°–37° C.

8. Method according to claim 1 wherein a $CO_2$-containing solution is introduced into the liquid mixture.

9. Method according to claim 8 wherein said $CO_2$-containing solution is formed during methane fermentation, recovered and recycled into the liquid mixture.

10. Method according to claim 8 wherein the $CO_2$-containing solution is compressed prior to introduction into the liquid mixture.

11. Method according to claim 1 wherein a phosphate buffer solution is added to the liquid mixture in an amount such as to adjust the pH thereof to between about 7.4 and 8.4.

12. Method according to claim 11 wherein said phosphate buffer solution comprises 0.2 mol aqueous KH$_2$PO$_4$ solution and 0.2 mol aqueous NaOH solution.

13. Method according to claim 12 wherein said buffer and said liquid mixture are mixed together in substantially the following volume relationship:

$$y+z=3X$$

wherein x represents a volume of the 0.2 mol aqueous KH$_2$PO$_4$ solution, y represents a volume of the 0.2 mol aqueous NaOH solution and z represents a volume of the liquid mixture.

* * * * *